United States Patent
Chang et al.

(10) Patent No.: US 12,111,259 B2
(45) Date of Patent: Oct. 8, 2024

(54) DETECTION KIT AND METHOD FOR DETECTING ABUSED DRUGS

(71) Applicants: National Taiwan University, Taipei (TW); Investigation Bureau, Ministry of Justice, New Taipei (TW)

(72) Inventors: Huan-Tsung Chang, Taipei (TW); Yao-Te Yen, Taipei (TW); Yin-Jue Chang, New Taipei (TW); Yuh-Lin Liu, New Taipei (TW)

(73) Assignees: National Taiwan University, Taipei (TW); Investigation Bureau, Ministry of Justice, New Taipei (TW)

( * ) Notice: Subject to any disclaimer, the term of this patent is extended or adjusted under 35 U.S.C. 154(b) by 162 days.

(21) Appl. No.: 17/580,571

(22) Filed: Jan. 20, 2022

(65) Prior Publication Data

US 2023/0076385 A1   Mar. 9, 2023

(30) Foreign Application Priority Data

Aug. 26, 2021   (TW) ................. 110131715

(51) Int. Cl.
| | | |
|---|---|---|
| *G01N 21/64* | (2006.01) | |
| *G01N 33/543* | (2006.01) | |
| *G01N 33/94* | (2006.01) | |

(52) U.S. Cl.
CPC ... *G01N 21/6428* (2013.01); *G01N 33/54388* (2021.08); *G01N 33/94* (2013.01); *G01N 2021/6432* (2013.01)

(58) Field of Classification Search
CPC ......... G01N 21/6428; G01N 33/54388; G01N 33/94; G01N 2021/6432; G01N 21/643; G01N 33/542; G01N 21/65; G01N 2021/7786; G01N 2201/0221
See application file for complete search history.

(56) References Cited

U.S. PATENT DOCUMENTS

| | | |
|---|---|---|
| 10,041,962 B1 | 8/2018 | Chang et al. |
| 2011/0039346 A1 | 2/2011 | Bradley et al. |
| 2012/0329168 A1 | 12/2012 | Lin et al. |
| 2016/0154015 A1 | 6/2016 | Stitzlein et al. |
| 2020/0225216 A1 | 7/2020 | Chang et al. |

FOREIGN PATENT DOCUMENTS

| | | |
|---|---|---|
| CN | 102879568 | 1/2013 |
| CN | 108203730 | 6/2018 |
| KR | 20130127878 | 11/2013 |
| TW | 201915488 | 4/2019 |
| TW | I663400 | 6/2019 |
| TW | M582590 | 8/2019 |
| TW | I682172 | 1/2020 |

OTHER PUBLICATIONS

"Office Action of Taiwan Counterpart Application", issued on Jul. 4, 2022, p. 1-p. 3.

*Primary Examiner* — Elizabeth C. Kemmerer
*Assistant Examiner* — McKenzie A Dunn
(74) *Attorney, Agent, or Firm* — JCIPRNET

(57) ABSTRACT

A detection kit suitable for detecting a target in a sample is provided. The detection kit includes a syringe, a first reaction container, a second reaction container, and a plurality of fluorescent substances. The syringe is loaded with first organic solvent. The first reaction container is connected to the syringe and is loaded with the sample. The second reaction container is connected to the first reaction container and is loaded with second organic solvent. The fluorescent substances are dispersed in the second organic solvent and emit fluorescence. When the target in the sample is dissolved in the first organic solvent and reacts with the fluorescent substances in the second organic solvent, the fluorescence emitted by the fluorescent substances is quenched.

4 Claims, 8 Drawing Sheets

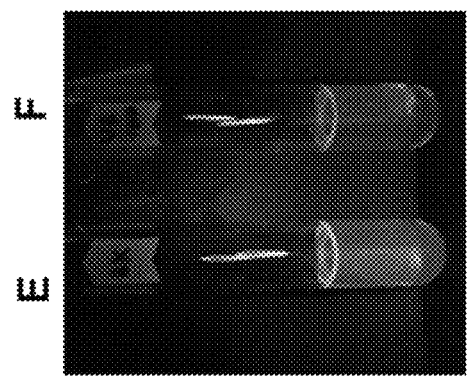
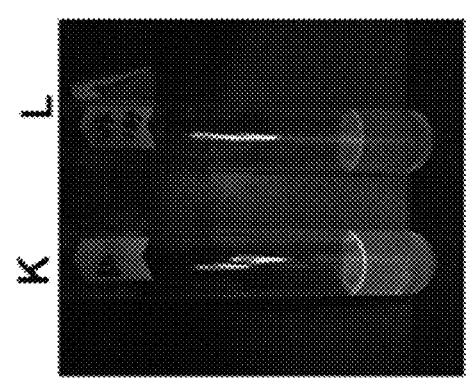
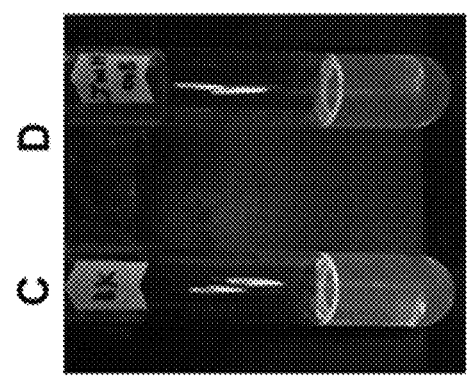
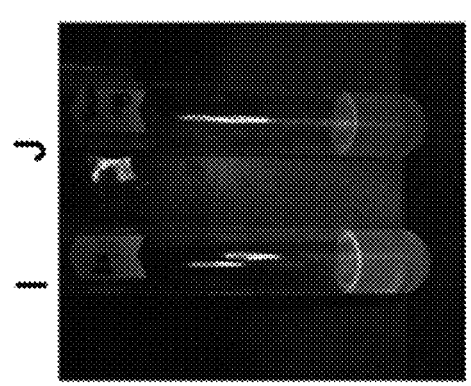
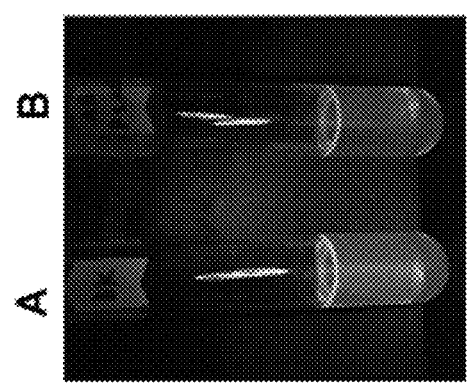
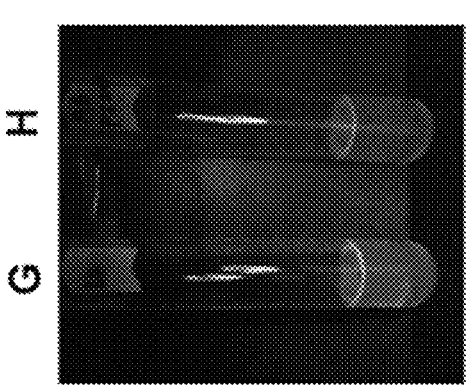
FIG. 4A
FIG. 4B

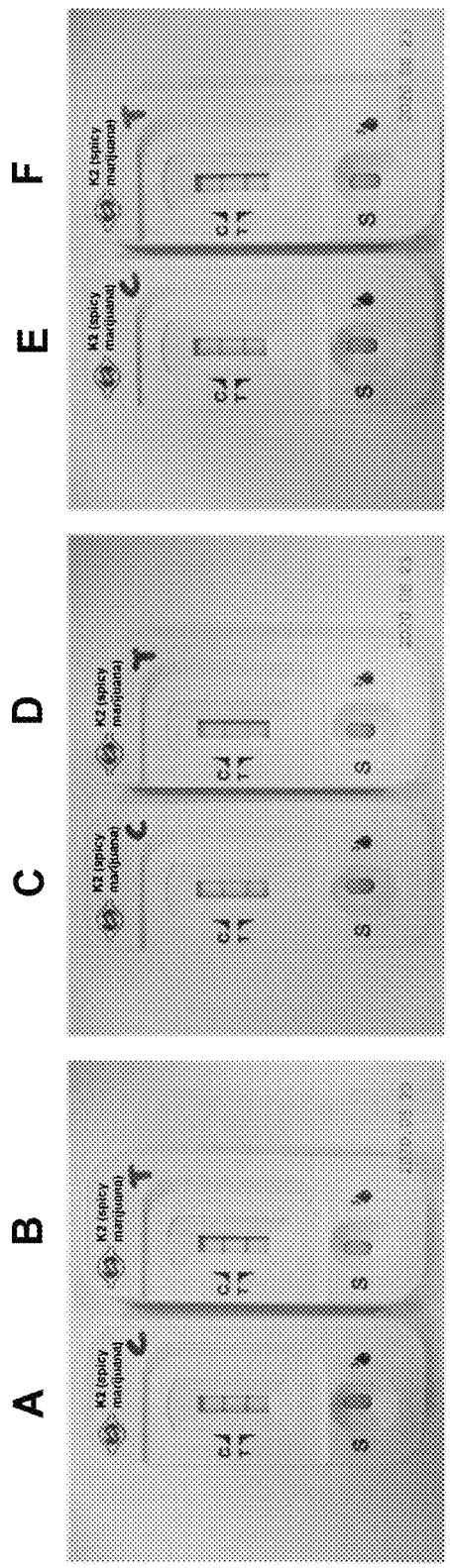
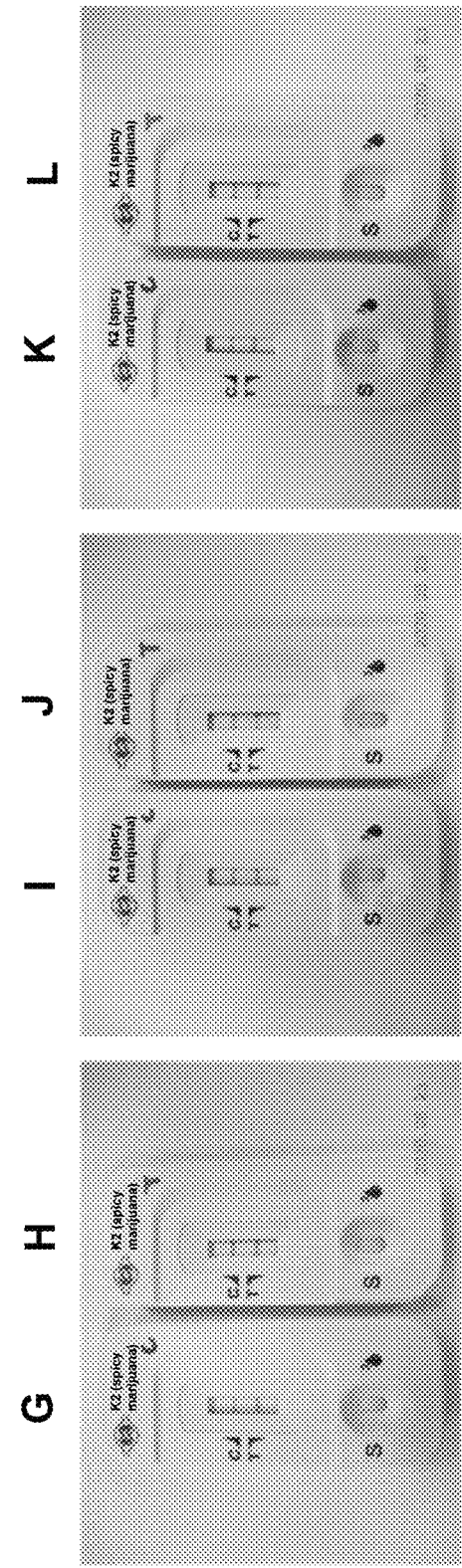
FIG. 7A
FIG. 7B

DETECTION KIT AND METHOD FOR DETECTING ABUSED DRUGS

CROSS-REFERENCE TO RELATED APPLICATION

This application claims the priority benefit of Taiwan application serial no. 110131715, filed on Aug. 26, 2021. The entirety of the above-mentioned patent application is hereby incorporated by reference herein and made a part of this specification.

BACKGROUND

Technical Field

The invention relates to a detection kit and a detection method, and particularly relates to a detection kit and a method for detecting abused drugs.

Description of Related Art

Synthetic *cannabis* drugs are currently one of the emerging drugs abused in nation. Therefore, it is necessary to have a tool used for rapid screening at an anti-drug scene. Although the current detection methods used to detect synthetic *cannabis* drugs include handheld Raman spectrometers, commercially available color reagents, commercially available immunoassay test papers, etc., the above detection methods still have problems such as poor sensitivity or selectivity, which leads to the risk of misjudgement. Therefore, there is an urgent need for a detection method that may solve the above shortcomings.

SUMMARY

The invention is directed to a detection kit and a method for detecting abused drugs, which have advantages of high selectivity and good sensitivity, thereby effectively reducing a false negative rate of detection.

The invention provides a detection kit suitable for detecting a target in a sample. The detection kit includes a syringe, a first reaction container, a second reaction container, and a plurality of fluorescent substances. The syringe is loaded with first organic solvent. The first reaction container is connected to the syringe and is loaded with the sample. The second reaction container is connected to the first reaction container and is loaded with second organic solvent. The fluorescent substances are dispersed in the second organic solvent and emit fluorescence. When the target in the sample is extracted by the first organic solvent and reacts with the fluorescent substances in the second organic solvent, the fluorescence emitted by the fluorescent substances is quenched.

In an embodiment of the invention, the first organic solvent and the second organic solvent include toluene, xylene, dimethyl sulfoxide, dimethyl formamide, chlorobenzene, chloroform or dichloromethane.

In an embodiment of the invention, the fluorescent substances are thiol-protected gold nanoclusters that the thiol ligand has a carbon chain number ranging from six to sixteen.

In an embodiment of the invention, a particle size of the fluorescent substances ranges from 1.02 nm to 2.36 nm.

In an embodiment of the invention, the fluorescence emitted by the fluorescent substances is orange-red fluorescence excited by ultraviolet light irradiation.

In an embodiment of the invention, the target includes a synthetic *cannabis* drug.

In an embodiment of the invention, a detection limit of the detection kit for the synthetic *cannabis* drug is 0.0087 mM.

The invention provides a method for detecting abused drugs, which is suitable for detecting an abused drug in a sample and includes following steps. The aforementioned detection kit is provided. The first organic solvent in the syringe is added to the first reaction container. The first organic solvent and the sample have a first reaction to obtain detection liquid. The detection liquid is added to the second reaction container, so that the detection liquid and the fluorescent substances in the second organic solvent have a second reaction. By irradiating the ultraviolet light, a quenching condition of the fluorescence emitted by the fluorescent substances in the second organic solvent is determined, where when there is the abused drug in the sample, the abused drug is extracted by the first organic solvent and reacts with the fluorescent substances in the second organic solvent, so that the fluorescence emitted by the fluorescent substances is quenched.

In an embodiment of the invention, a reaction time of the first reaction is 1 second to 5 seconds.

In an embodiment of the invention, the method for detecting abused drugs further includes a method for confirming a concentration of the abused drug in the detection liquid according to the quenching condition, and includes following steps. A series of the abused drug with known concentrations is provided in the second reaction container of the detection kit. After the abused drug reacts with the fluorescent substances in the second organic solvent, the fluorescent substances are irradiated by the ultraviolet light. A fluorescence intensity of the abused drug at each concentration is determined to establish a linear relationship between a standard concentration and a relative fluorescence quenching rate. The quenching condition is determined based on the linear relationship between the standard concentration and the relative fluorescence quenching rate to confirm a concentration of the abused drug in the detection liquid.

Based on the above description, in the detection kit and the method for detecting abused drugs of the embodiment of the invention, the detection kit includes a syringe, a first reaction container, a second reaction container, and a plurality of fluorescent substances. The syringe is loaded with first organic solvent. The first reaction container is connected to the syringe and is loaded with a sample. The second reaction container is connected to the first reaction container and is loaded with second organic solvent, and the fluorescent substances are dispersed in the second organic solvent and emit fluorescence. When there is an abused drug in the sample, the abused drug in the sample is extracted by the first organic solvent and reacts with the fluorescent substances in the second organic solvent, so that the fluorescence emitted by the fluorescent substances is quenched. Namely, whether the abused drug exists in the sample is determined according to a quenching condition of the fluorescence. In this way, the detection kit and the method for detecting abused drugs of the embodiment have the advantages of high selectivity and good sensitivity, thereby effectively reducing a false negative rate of detection.

To make the aforementioned more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 4A and FIG. 4B are fluorescence change diagrams of using the detection kit to detect cigarettes or rose tea containing and not containing synthetic *cannabis* drugs according to an embodiment of the invention.

FIG. 7A and FIG. 7B are detection results of using commercially available immunoassay test paper to detect cigarettes or rose tea containing and not containing synthetic *cannabis* drugs.

DESCRIPTION OF THE EMBODIMENTS

Figure 1A:
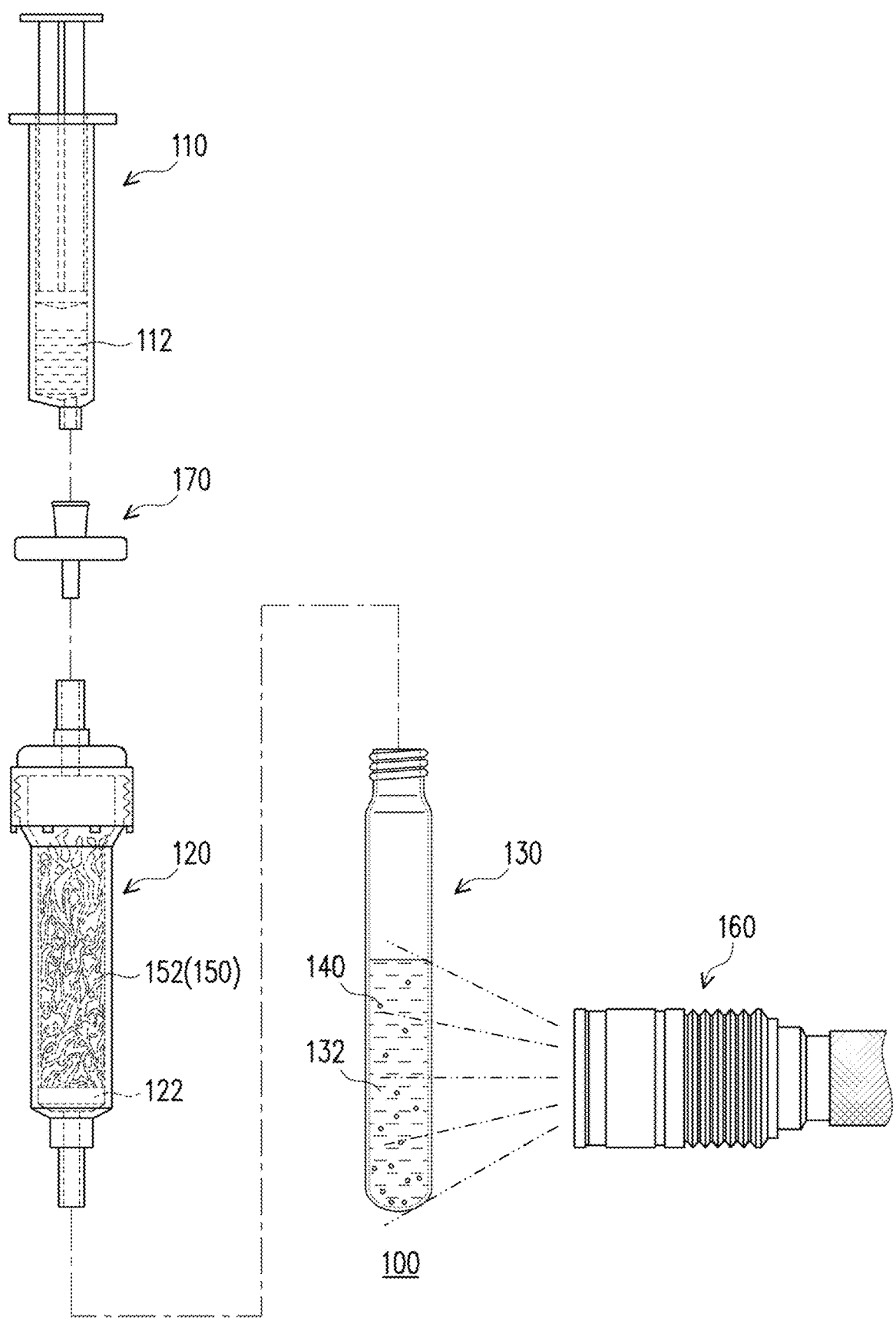
FIG. 1A is a schematic diagram of a detection kit according to an embodiment of the invention.

FIG. 1A is a schematic diagram of a detection kit according to an embodiment of the invention. Referring to FIG. 1A, the detection kit 100 of the embodiment includes a syringe 110, a first reaction container 120, a second reaction container 130, and a plurality of fluorescent substances 140. The syringe 110 is loaded with first organic solvent 112. The first reaction container 120 is connected to the syringe 110 and is loaded with a sample 150. The second reaction container 130 is connected to the first reaction container 120 and is loaded with second organic solvent 132. The plurality of fluorescent substances 140 are dispersed in the second organic solvent 132 and emit fluorescence. The sample 150 is loaded on a filter pad 122 in the first reaction container 120 to prevent the sample 150 from entering the second reaction container 130 during detection to interfere a detection result. In the embodiment, the detection kit 100 is suitable for detecting a target 152 in the sample 150. Therefore, when the target 152 in the sample 150 is extracted by the first organic solvent 112 and reacts with the fluorescent substances 140 in the second organic solvent 132, the fluorescence emitted by the fluorescent substances 140 will be quenched.

To be specific, in the embodiment, the first organic solvent 112 and the second organic solvent 132 include toluene, xylene, dimethyl sulfoxide, dimethyl formamide, chlorobenzene, chloroform, dichloromethane or other suitable organic solvents, but the invention is not limited thereto. The target 152 is, for example, synthetic *cannabis* drugs, but the invention is not limited thereto. The synthetic *cannabis* drugs, for example, include AB-PINACA, AM-2201, JWH-018, JWH-073, JWH-250, UR-144, and XLR-11, but the invention is not limited thereto. The sample 150 is, for example, a cigarette or scented tea mixed with the synthetic *cannabis* drugs, but the invention is not limited thereto. The fluorescent substances 140 may be thiol-protected gold nanoclusters that the thiol ligand has a carbon chain number ranging from six to sixteen, for example, hexanethiol-protected gold nanocluster, decanthiol-protected gold nanoclusters, hexadecanethiol-protected gold nanoclusters, or other long carbon chain thiol-protected gold nanoclusters or other fluorescent substances suitable for detecting the synthetic *cannabis* drugs, but the invention is not limited thereto. The fluorescent substances 140 of the embodiment may be irradiated by ultraviolet light of an ultraviolet light source 160 to emit fluorescence, such as orange-red fluorescence, but the invention is not limited thereto. However, when the fluorescent substances 140 react with the synthetic *cannabis* drugs, a fluorescence intensity of the orange-red fluorescence emitted by the fluorescent substances 140 will be weakened, or even the fluorescence may be quenched.

To be specific, in the embodiment, a method for detecting abused drugs is also provided for the above-mentioned detection kit 100, which includes the following steps. First, the detection kit 100 is provided. Then, the first organic solvent 112 in the syringe 110 is added to the first reaction container 120, such that the first organic solvent 112 and the sample 150 have a first reaction to obtain detection liquid. Where, a reaction time of the first reaction is 1 second to 5 seconds to avoid the first organic solvent 112 from dissolving out components other than the target 152 in the sample 150 (for example, a base material of tobacco or tea itself) due to a long reaction time to interfere a detection result. Then, the detection liquid is added to the second reaction container 130, so that the detection liquid and the fluorescent substances 140 in the second organic solvent 132 have a second reaction. Finally, by irradiating the ultraviolet light of the ultraviolet light source 160, a quenching condition of the fluorescence emitted by the fluorescent substances 140 in the second organic solvent 132 is determined. Therefore, when there is an abused drug in the sample 150, the abused drug may be dissolved in the first organic solvent 112 and reacts with the fluorescent substances 140 in the second organic solvent 132, so that the fluorescence emitted by the fluorescent substances 140 is quenched.

Moreover, in the embodiment, the detection kit 100 may also selectively include a filter 170 disposed between the syringe 110 and the first reaction container 120. In detail, the filter 170 has two openings, where one opening is connected to the syringe 110 and the other opening is connected to the first reaction container 120. The filter 170 may be used to prevent the first organic solvent 112 in the syringe 110 from flowing into the first reaction container 120 before being injected into the first reaction container 120. In this way, it is avoided that the first organic solvent 112 reacts with the sample 150 for a too long time to dissolve out components other than the target 152 in the sample 150 (for example, the base material of tobacco or tea itself) to interfere the detection result. In the embodiment, the filter 170 may be, for example, a filter membrane with a pore size of 0.2 μm, but the invention is not limited thereto.

Drawings and embodiments are provided below to illustrate the technical means adopted by the invention for achieving the purpose.

EXPERIMENTAL EXAMPLE

Experimental Example 1: Preparation of Fluorescent Substances

After a thiol compound and methyl triphenylphosphonium gold ($CH_3AuPPh_3$) dissolved in o-xylene solvent were heated in an oil bath at 90-140° C. for 20-60 minutes, the heating was stopped and the above materials were placed at room temperature for 18 hours, after cooling down, purification was performed in a manner of centrifugation (8,000 rpm, 3 min) to obtain fluorescent substances. Then, the purified fluorescent substances were dissolved in chloroform or other suitable organic solvents for storage. The thiol compound was used as a reducing agent and a protecting group. The thiol compound was, for example, 1-hexanethiol, 1-decanthiol, or 1-hexadecanethiol. A concentration of the $CH_3AuPPh_3$ was, for example, 0.8 mg/mL (or 1.68 mM). A molar ratio of the thiol compound and the $CH_3AuPPh_3$ was, for example, 2:1, 8:1, 16:1, 32:1, 64:1, or 128:1. The fluorescent substances were, for example, hexanethiol-protected gold nanoclusters, decanthiol-protected gold nanoclusters, hexadecanethiol-protected gold nanoclusters. A concentration of the fluorescent substances dissolved in chloroform was, for example, 10 mg/mL, but the invention is not limited thereto.

Experimental Example 2: Identification of Prepared Fluorescent Substances

The following fluorescent substances were, for example, decanthiol-protected gold nanoclusters. First, the decanthiol-protected gold nanoclusters were identified by X-ray photoelectron spectroscopy (XPS), signals were found to be generated at 84.6 eV, 88.6 eV, 162.9 eV, and 284.5 eV. The signals of 84.6 eV and 88.6 eV represented gold atoms, the signal of 162.9 eV represented sulfur atoms, and the signal of 284.5 eV represented carbon atoms. Therefore, the decanthiol-protected gold nanoclusters had indeed formed stably.

Figure 1B:
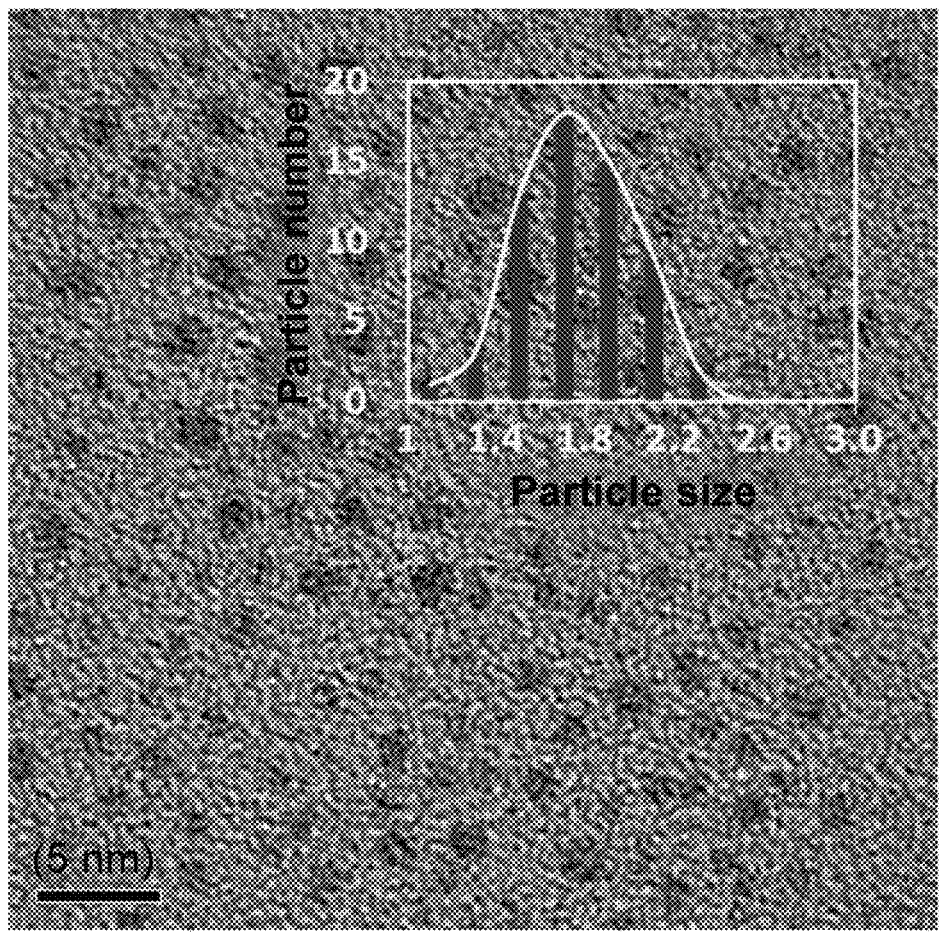
FIG. 1B is a TEM image of fluorescent substances in a detection kit and a relationship diagram of a particle number and a particle size of the fluorescent substances according to an embodiment of the invention.

FIG. 1B is a TEM image of the fluorescent substances in a detection kit and a relationship diagram of a particle number and a particle size of the fluorescent substances according to an embodiment of the invention. Referring to FIG. 1B, the decanthiol-protected gold nanoclusters were observed by using a transmission electron microscope (TEM), and then the particle number and particle size of the decanthiol-protected gold nanoclusters were calculated to illustrate the relationship diagram of the particle number and the particle size. The particle sizes of the decanthiol-protected gold nanocluster were, for example, between 1.02 to 2.36 nm, and an average particle size was 1.75 nm, which represented that the synthetic decanthiol-protected gold nanoclusters (particle) had a uniform particle size and a narrow particle size range.

Figure 2A:
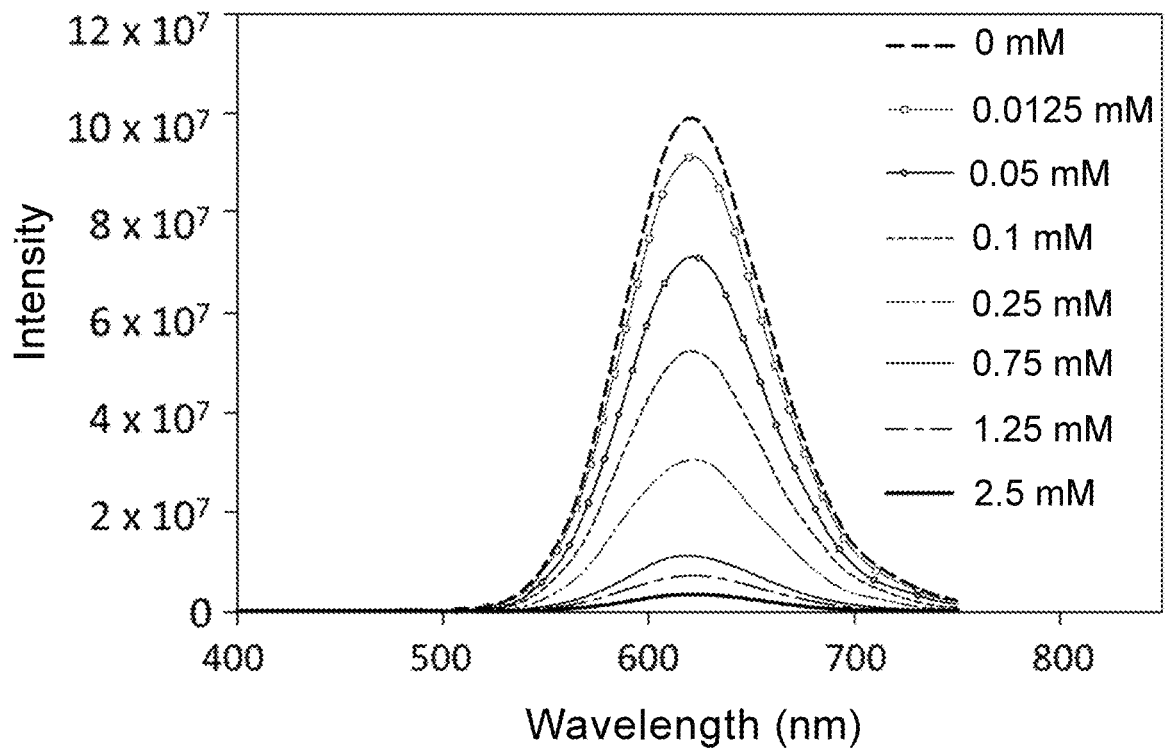
FIG. 2A is a diagram illustrating fluorescence intensity changes after reaction of a detection kit with different concentrations of synthetic *cannabis* drug according to an embodiment of the invention.
Figure 2B:
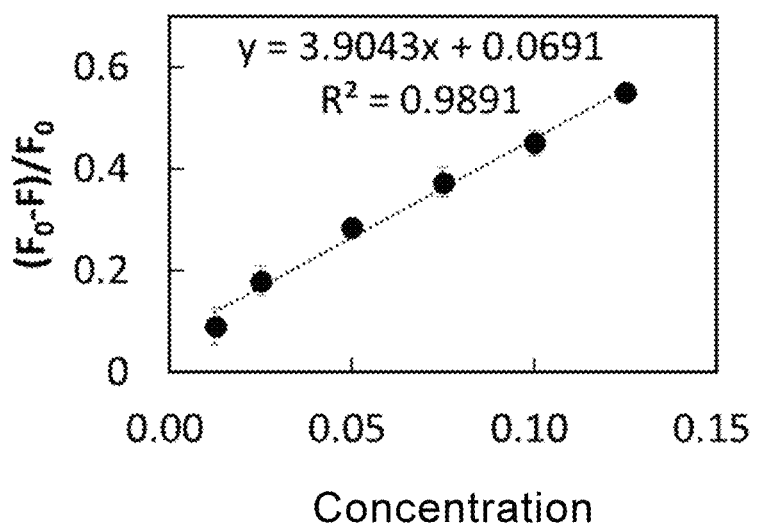
FIG. 2B is a diagram illustrating a linear relationship between concentration and a relative fluorescence quenching rate established after reaction of the detection kit with different concentrations of the synthetic *cannabis* drug according to an embodiment of the invention.

Experimental Example 3: Analysis of Fluorescence Intensity Changes after Reaction of Decanthiol-Protected Gold Nanoclusters and Synthetic *Cannabis* Drug FIG. 2A is a diagram illustrating fluorescence intensity changes after reaction of the detection kit with different concentrations of synthetic *cannabis* drug. FIG. 2B is a diagram illustrating a linear relationship between concentration and a relative fluorescence quenching rate established after reaction of the fluorescent substances of FIG. 2A with different concentrations of the synthetic *cannabis* drug.

Referring to FIG. 2A, in the embodiment, the decanthiol-protected gold nanoclusters that had not reacted with the synthetic *cannabis* drug (0 mM) were used as a control group. Under ultraviolet light, a fluorescence intensity of the orange-red fluorescence of the decanthiol-protected gold nanoclusters was detected to be about $10 \times 10^7$ (shown by the dotted lines in FIG. 2A). Then, the different concentrations of synthetic *cannabis* drug (0.0125, 0.05, 0.1, 0.25, 0.75, 1.25, 2.5 mM) were reacted with the decanthiol-protected gold nanoclusters, respectively, and under the ultraviolet light. Fluorescence intensity change of the orange-red fluorescence of the decanthiol-protected gold nanoclusters reacted with different concentrations of the synthetic *cannabis* drug (0.0125, 0.05, 0.1, 0.25, 0.75, 1.25, 2.5 mM) were detected. In the embodiment, a wavelength range of the ultraviolet light was 280 nm to 380 nm, and a wavelength of the orange-red fluorescence was about 620 nm. The synthetic *cannabis* drug used here was, for example, UR-144.

From the results of FIG. 2A, it was learnt that as the concentration of the UR-144 increased (from 0.0125 mM to 2.5 mM), the fluorescence intensity of the orange-red fluorescence of the decanthiol-protected gold nanoclusters reacted with the UR-144 also gradually decreased significantly. Even the detected fluorescence intensity of the orange-red fluorescence almost approached 0 after the decanthiol-protected gold nanoclusters were reacted with 2.5 mM of UR-144. Therefore, the synthetic *cannabis* drug (such as UR-144) indeed quenched the orange-red fluorescence emitted by the decanthiol-protected gold nanoclusters in this embodiment. Therefore, synthetic *cannabis* drug was detected by observing the intensity change (or a quenching condition) of the orange-red fluorescence emitted by the decanthiol-protected gold nanoclusters.

Then, referring to FIG. 2B, a series of known UR-144 with different concentrations (0.0125, 0.025, 0.05, 0.075, 0.1, 0.125 mM) were reacted with the detection kit of the embodiment, and the fluorescence intensity of the orange-red fluorescence of the decanthiol-protected gold nanoclusters after the reaction was detected to calculate and illustrate the linear relationship between the concentration and the relative fluorescence quenching rate. To be specific, the relative fluorescence quenching rate is $(F_0-F)/F_0$, where $F_0$ is a value of the fluorescence intensity of the orange-red fluorescence after the decanthiol-protected gold nanoclusters react with 0 mM of UR-144, and F is a value of the fluorescence intensity of the orange-red fluorescence after the decanthiol-protected gold nanoclusters react with the different concentrations of UR-144 (0.0125, 0.025, 0.05, 0.075, 0.1, 0.125 mM). Therefore, the higher the concentration of the UR-144, the lower the value F representing the fluorescence intensity, and the higher the calculated relative fluorescence quenching rate $(F_0-F)/F_0$, as shown in FIG. 2B. In the embodiment, a calibration curve was drawn based on a linear range of FIG. 2B (for example, from a concentration of 0.0125 mM to 0.125 mM), and an equation (y=3.90x+ 0.07, a coefficient $R^2$ is 0.99) represented by the calibration curve was used to deduce that a limit of detection (LOD) of the fluorescent substances in the detection kit for the UR-144 was 0.0087 mM. Therefore, it was represented that the detection kit 100 containing the decanthiol-protected gold nanoclusters had high sensitivity for identifying synthetic *cannabis* drugs and effectively reduced the false negative rate of detection.

In the embodiment, when the detection kit was used to detect the synthetic *cannabis* drug with unknown concentration, the relative fluorescence quenching rate of X was calculated based on the fluorescence intensity change (or the quenching condition) after detection, and then the linear relationship diagram of the concentration and the relative fluorescence quenching rate established above was used to deduce the corresponding concentration when the relative fluorescence quenching rate is X.

Then, in the embodiment, the fluorescent intensity value of the orange-red fluorescence after reaction between the decanthiol-protected gold nanoclusters and other synthetic *cannabis* drugs was detected in a manner similar to that shown in FIG. 2A and FIG. 2B. Then, the linear relationship between the concentration and the relative fluorescence quenching rate (not shown) were calculated and illustrated, and then the calibration curve was used to deduce a detection limit of the fluorescent substances to other synthetic *cannabis* drugs. Table 1 respectively lists a linear range of calibration curve and a detection limit of synthetic *cannabis* drugs AB-PINACA and JWH-018.

TABLE 1

| Synthetic cannabis drugs | Linear range of calibration curve | Detection limit |
|---|---|---|
| AB-PINACA | 0.025 mM-0.25 mM | 0.0166 mM |
| JWH-018 | 0.0125 mM-0.125 mM | 0.0087 mM |

Figure 3:
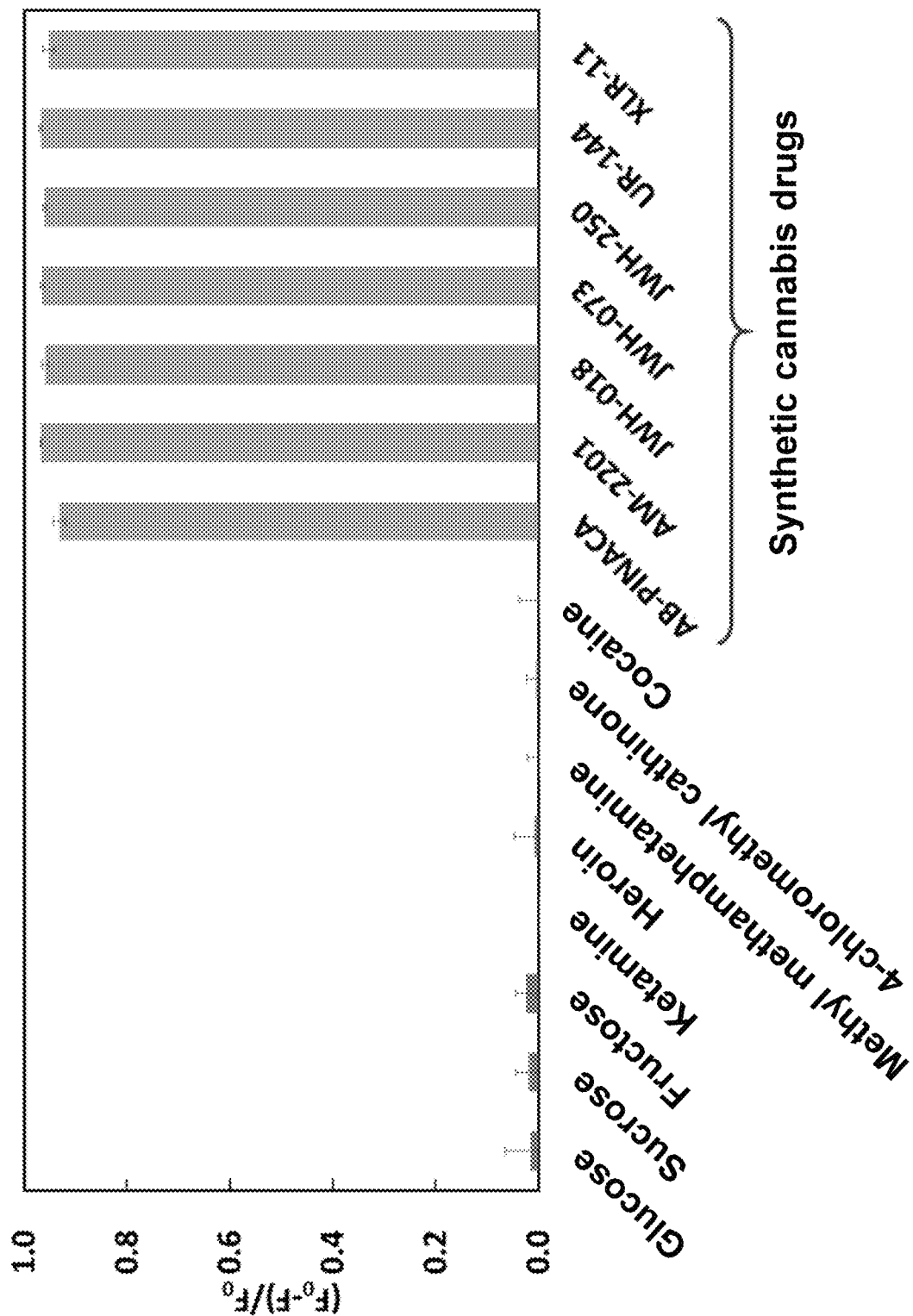
FIG. 3 illustrates relative fluorescence quenching rates after the detection kit reacts with different abused drugs or adulterants according to an embodiment of the invention.

Experimental Example 4: Selectivity Test of Decanthiol-Protected Gold Nanoclusters FIG. 3 illustrates relative fluorescence quenching rates after the detection kit reacts with different abused drugs or adulterants according to an embodiment of the invention. Referring to FIG. 3, the decanthiol-protected gold nanoclusters were respectively reacted with adulterants, non-synthetic *cannabis* drugs or synthetic *cannabis* drugs, and then the fluorescence intensities of the orange-red fluorescence after the reactions were detected to calculate values of the relative fluorescence quenching rates $(F_0-F)/F_0$. The adulterants included glucose, sucrose, and fructose. Non-synthetic *cannabis* drugs included ketamine, heroin, methamphetamine, 4-chloromethcathinone, and cocaine. The synthetic *cannabis* drugs included AB-PINACA, AM-2201, JWH-018, JWH-073, JWH-250, UR-144 and XLR-11. A test concentration of the non-synthetic *cannabis* drugs, the synthetic *cannabis* drugs, and the adulterants was 2.5 mM.

According to the results of FIG. 3, compared to the values (about 0 to 0.1) of the relative fluorescence quenching rates obtained after that the decanthiol-protected gold nanoclusters were reacted with glucose, sucrose, fructose, ketamine, heroin, methamphetamine, 4-chloromethcathinone, or cocaine, the values (about 0.95 or more) of the relative fluorescence quenching rates obtained after that the decanthiol-protected gold nanoclusters were reacted with AB-PINACA, AM-2201, JWH-018, JWH-073, JWH-250, UR-144 or XLR-11 were obviously higher. Therefore, when the synthetic *cannabis* drugs reacted with the decanthiol-protected gold nanoclusters, the orange-red fluorescence of the decanthiol-protected gold nanoclusters was quenched, but when the adulterants or the non-synthetic *cannabis* drugs reacted with the decanthiol-protected gold nanoclusters, the orange-red fluorescence of the decanthiol-protected gold nanoclusters was not quenched. Therefore, the detection kit 100 containing the decanthiol-protected gold nanoclusters had high selectivity for identifying the synthetic *cannabis* drugs and effectively reduced the false negative rate of detection.

Experimental Example 5: Comparison Between the Detection Kit of the Embodiment and Other Detection Methods for Detecting Synthetic *Cannabis* Drugs In the following description, the detection kit, a handheld Raman spectrometer, a commercially available color reagent, and a commercially available immunoassay test paper were respectively used to detect different samples. The samples included cigarette without doping AB-PINACA (indicated as a sample A), cigarette doped with 0.3% (weight percentage) of AB-PINACA (indicated as a sample B), and cigarette without doping JWH-018 (indicated as a sample C), cigarette doped with 0.3% of JWH-018 (indicated as a sample D), cigarette without doping UR-144 (indicated as a sample E), cigarette doped with 0.3% of UR-144 (indicated as a sample F), rose tea without doping AB-PINACA (indicated as a sample G), rose tea doped with 0.3% of AB-PINACA (indicated as a sample H), rose tea without doping JWH-018 (indicated as a sample I), rose tea doped with 0.3% of JWH-018 (indicated as a sample J), rose tea without doping UR-144 (indicated as a sample K) and rose tea doped with 0.3% of UR-144 (indicated as a sample L).

Example 1

FIG. 4A and FIG. 4B are fluorescence change diagrams of using the detection kit to detect cigarettes or rose tea containing and not containing synthetic *cannabis* drugs according to an embodiment of the invention. Referring to FIG. 4A and FIG. 4B, the detection kit 100 of the embodiment was used to respectively detect samples A-L to determine whether the samples A-L contain synthetic *cannabis* drugs. To be specific, the detection was carried out according to the method for detecting abused drugs provided in the embodiment, for example, the method included following steps, but the invention is not limited thereto. First, the detection kit 100 as shown in FIG. 1A was provided, a syringe (the syringe 110), a syringe filter (the filter 170), a sample tube containing a filter gasket (the first reaction container 120), and a glass test tube (the second reaction container 130) were sequentially connected and assembled. The syringe was loaded with about 1 mL to 5 mL of toluene, the sample tube was loaded with the sample 150, and the glass test tube was loaded with the decanthiol-protected gold nanoclusters 140 dispersed in chloroform. Then, the toluene in the syringe was injected into the sample tube, so that the toluene and the sample had a first reaction (a reaction time is 1 second to 5 seconds). At this time, if the sample was doped with synthetic *cannabis* drugs, the toluene might extract the synthetic *cannabis* drugs to obtain detection liquid containing the synthetic *cannabis* drugs. Thereafter, the detection liquid was added to the glass test tube, so that the detection liquid and the decanthiol-protected gold nanoclusters in chloroform had a second reaction. Finally, ultraviolet light emitted by a handheld ultraviolet flashlight (280 nm or 302 nm) was used to irradiate the glass test tube containing the decanthiol-protected gold nanoclusters to determine a quenching condition of the orange-red fluorescence emitted by the decanthiol-protected gold nanoclusters after reaction with the detection liquid.

From the results of FIG. 4A and FIG. 4B, under the irradiation of the ultraviolet light, the orange-red fluorescence was all observed with naked eyes from the samples A, C, E, G, I, and K that were not doped with the synthetic *cannabis* drugs, but the orange-red fluorescence was not observed from the samples B, D, F, H, J, and L doped with the synthetic *cannabis* drugs. It means that the samples B, D, F, H, J, and L doped with the synthetic *cannabis* drugs significantly quenched the orange-red fluorescence emitted by the decanthiol-protected gold nanoclusters in the detection kit, which was easily recognized by the naked eyes.

Comparative Example 1

Figure 5A:
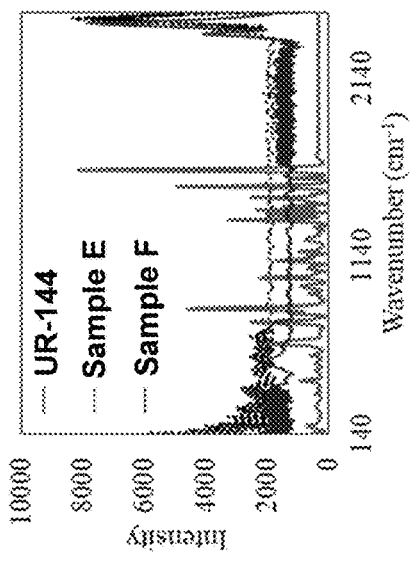
FIG. 5A and FIG. 5B are Raman spectrograms of using a Raman spectrometer to detect cigarettes or rose tea containing and not containing synthetic *cannabis* drugs and pure powder synthetic *cannabis* drugs.
Figure 5A:
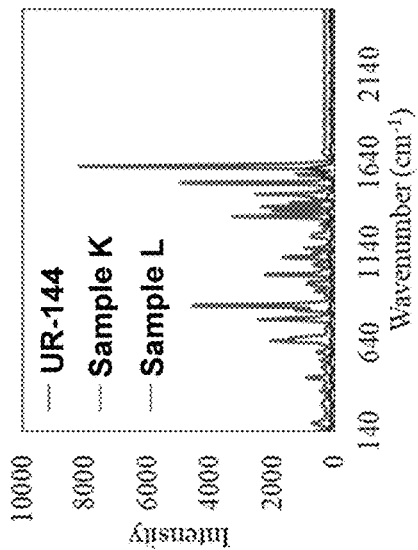
Figure 5B:
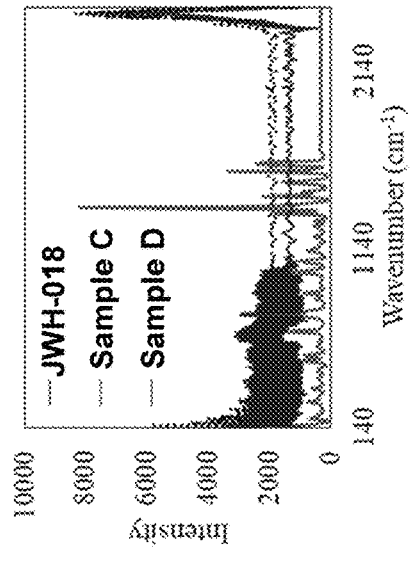
Figure 5B:
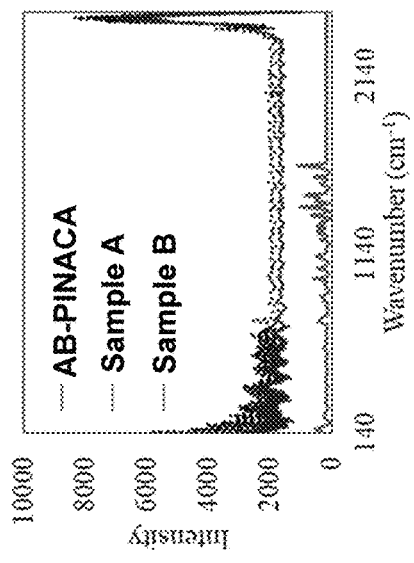
Figure 5B:
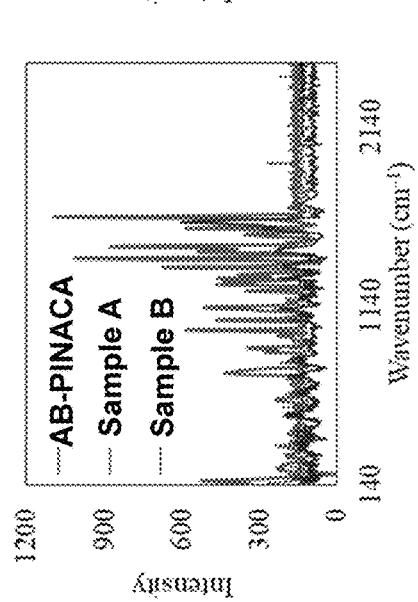

FIG. 5A and FIG. 5B are Raman spectrograms of using a Raman spectrometer to detect cigarettes or rose tea containing and not containing synthetic *cannabis* drugs and pure powder synthetic *cannabis* drugs. Referring to FIG. 5A and FIG. 5B, a handheld Raman spectrometer was used to respectively irradiate the samples A-L and standard substances of the synthetic *cannabis* drugs (indicated as AB-PINACA, JWH-018, UR-144) to detect whether the samples A-L contained the synthetic *cannabis* drugs.

According to the results of FIG. 5A and FIG. 5B, under the detection of the handheld Raman spectrometer, by comparing with signals of the standard substances of the synthetic *cannabis* drugs (indicated as AB-PINACA, JWH-018, UR-144), in the signals of the samples A, C, E, G, I, and K that were not doped with the synthetic *cannabis* drugs, signals of the synthetic *cannabis* drugs were indeed not observed, but in the signals of the samples B, D, F, H, J, and L doped with the synthetic *cannabis* drugs, only signals of cigarettes or rose tea were observed, and signals of the synthetic *cannabis* drugs were not observed (i.e., false negative), which represented that it was impossible to use the handheld Raman spectrometer to distinguish the samples A, C, E, G, I, K that were not doped with the synthetic *cannabis* drugs and the samples B, D, F, H, J that were doped with the synthetic *cannabis* drugs. In other words, it was impossible to use the handheld Raman spectrometer to detect whether cigarette or rose tea was doped with the synthetic *cannabis* drugs.

Comparative Example 2

Figure 6A:
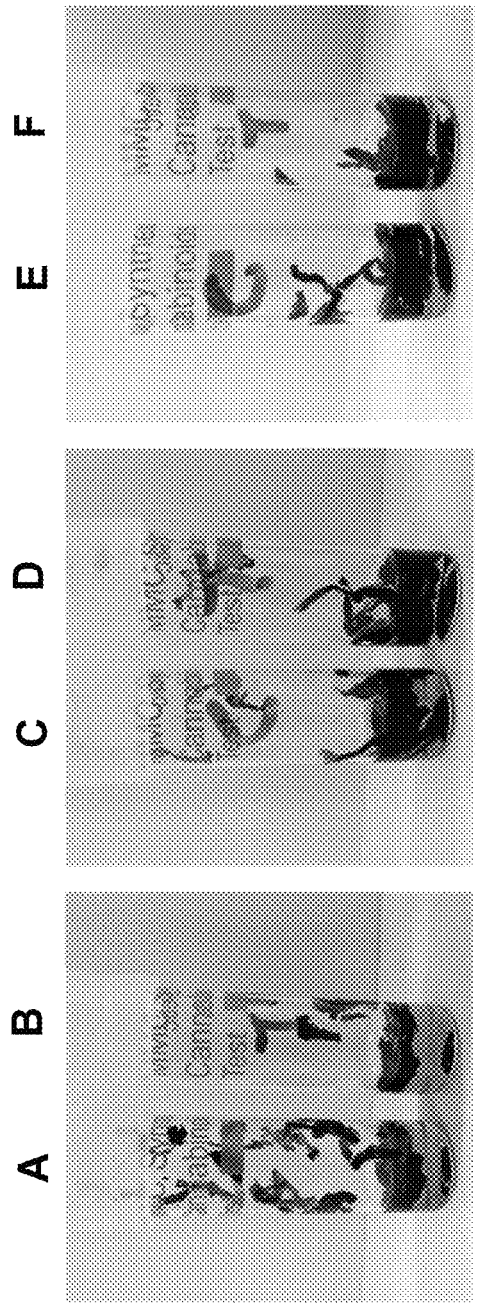
FIG. 6A and FIG. 6B illustrate the use of commercially available color reagent to detect color changes of cigarettes or rose tea containing and not containing synthetic *cannabis* drugs.
Figure 6B:
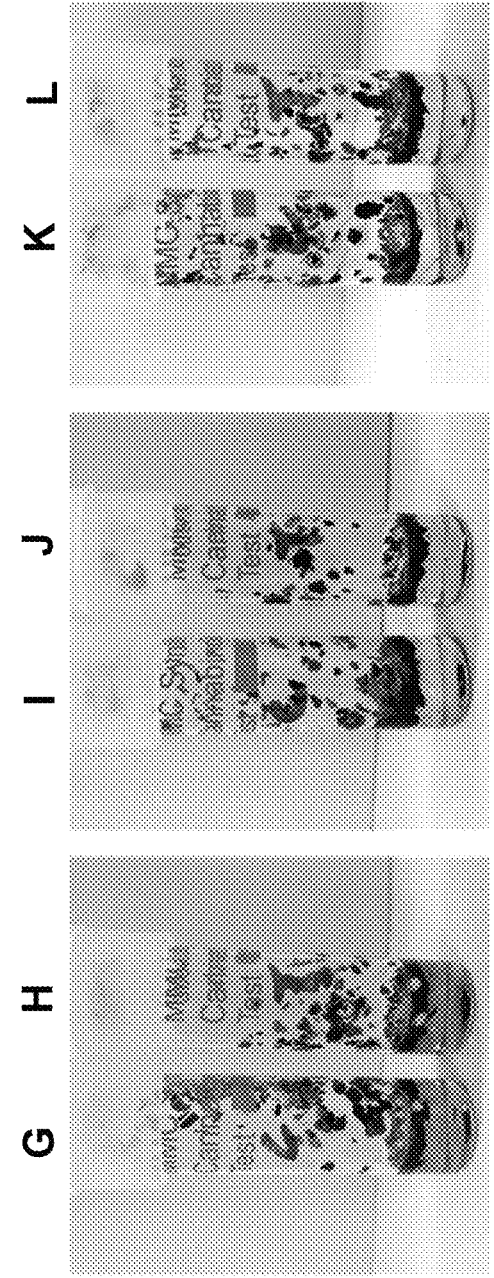

FIG. 6A and FIG. 6B illustrate the use of commercially available color reagent to detect cigarettes or rose tea containing and not containing synthetic *cannabis* drugs. Referring to FIG. 6A and FIG. 6B, the commercially available color reagent was used to respectively detect the samples A-L to determine whether the samples A-L contained the synthetic *cannabis* drugs.

According to the results of FIG. 6A and FIG. 6B, after the commercially available color reagent was respectively reacted with the samples A-L, in the samples A, C, E, G, I, and K that were not doped with the synthetic *cannabis* drugs, it was observed with naked eyes that the reacted reagent presented a light yellow color or a yellow color, and in the samples B, D, F, H, J, and L doped with the synthetic *cannabis* drugs, it was also observed with naked eyes that the reacted reagent presented the light yellow color or the yellow color, which represented that it was impossible to use the commercially available color reagent to distinguish the samples A, C, E, G, I, K that were not doped with the synthetic *cannabis* drugs and the samples B, D, F, H, J that were doped with the synthetic *cannabis* drugs. In other words, it was impossible to use the commercially available color reagents to detect whether the cigarette or rose tea was doped with the synthetic *cannabis* drugs.

Comparative Example 3

FIG. 7A and FIG. 7B are detection results of using commercially available immunoassay test paper to detect cigarettes or rose tea containing and not containing synthetic *cannabis* drugs. Referring to FIG. 7A and FIG. 7B, the commercially available immunoassay test papers were used to respectively detect the samples A-L to determine whether the samples A-L contained synthetic *cannabis* drugs.

From the results of FIG. 7A and FIG. 7B after the commercially available immunoassay test papers were respectively reacted with the samples A-L, in the samples A, C, E, G, I, and K that were not doped with synthetic *cannabis* drugs, color bands (negative results) was observed with naked eyes on positions of scales C and T of the test paper after the reaction, and in the samples B, D, F, H, J, and L doped with synthetic marijuana drugs, color bands (i.e., false negatives) was also observed on positions of the scales C and T of the test paper after the reaction. Therefore, it was impossible to use commercially available immunoassay test papers to distinguish the samples A, C, E, G, I, K that were not doped with synthetic *cannabis* drugs and the samples B, D, F, H, J, L that were doped with synthetic *cannabis* drugs. In other words, it was impossible to use the commercially available immunoassay test papers to detect whether cigarettes or rose tea were doped with synthetic *cannabis* drugs.

Therefore, according to the results of Example 1, Comparative Example 1, Comparative Example 2, and Comparative Example 3, it may be confirmed that compared to the detection methods of using the handheld Raman spectrometer, the commercially available color reagent, and the commercially available immunoassay test paper, the detection kit of the embodiment may quickly identify the synthetic *cannabis* drugs doped in cigarettes or rose tea.

In summary, in the detection kit and the method for detecting abused drugs of the embodiment of the invention, the detection kit includes a syringe, a first reaction container, a second reaction container, and a plurality of fluorescent substances. The syringe is loaded with first organic solvent. The first reaction container is connected to the syringe and is loaded with a sample. The second reaction container is connected to the first reaction container and is loaded with second organic solvent, and the fluorescent substances are dispersed in the second organic solvent and emit fluorescence. When there is an abused drug in the sample, the abused drug in the sample is extracted by the first organic solvent and reacts with the fluorescent substances in the second organic solvent, so that the fluorescence emitted by the fluorescent substances is quenched. Namely, whether the abused drug exists in the sample is determined according to a quenching condition of the fluorescence. In this way, the detection kit and the method for detecting abused drugs of the embodiment have the advantages of high selectivity and good sensitivity, thereby effectively reducing a false negative rate of detection.

It will be apparent to those skilled in the art that various modifications and variations can be made to the disclosed embodiments without departing from the scope or spirit of the invention. In view of the foregoing, it is intended that the invention covers modifications and variations provided they fall within the scope of the following claims and their equivalents.

What is claimed is:

1. A detection kit, suitable for detecting a target in a sample, comprising:
    a syringe, loaded with first organic solvent;
    a first reaction container, connected to the syringe and loaded with the sample;
    a second reaction container, connected to the first reaction container and loaded with second organic solvent; and a plurality of fluorescent substances, dispersed in the second organic solvent, wherein when the target in the sample is extracted by the first organic solvent and reacts with the fluorescent substances in the second organic solvent, the fluorescence emitted by the fluorescent substances is quenched, wherein the target comprises a synthetic *cannabis* drug, and the fluorescent substances are decanethiol-protected gold nanoclusters.

2. The detection kit as claimed in claim 1, wherein the first organic solvent comprises toluene, xylene, dimethyl sulfoxide, dimethyl formamide, chlorobenzene, chloroform, or dichloromethane;

wherein the second organic solvent comprises toluene, xylene, dimethyl sulfoxide, dimethyl formamide, chlorobenzene, chloroform, or dichloromethane.

3. The detection kit as claimed in claim 1, wherein particle sizes of the fluorescent substances range from 1.02 nm to 2.36 nm.

4. The detection kit as claimed in claim 1, wherein the fluorescence emitted by the fluorescent substances is orange-red fluorescence excited by ultraviolet light irradiation.

* * * * *